US008999350B2

(12) United States Patent
Loret (10) Patent No.: US 8,999,350 B2
(45) Date of Patent: Apr. 7, 2015

(54) MODIFIED TAT OYI PROTEIN WITH ENHANCED IMMUNOGENICITY (75) Inventor: Erwann Loret, La Ciotat (FR)

(73) Assignee: Universite d'Aix-Marseille, Marseille (FR)

(*) Notice: Subject to any disclaimer, the term of this patent is extended or adjusted under 35 U.S.C. 154(b) by 1001 days.

(21) Appl. No.: 12/989,165

(22) PCT Filed: Apr. 22, 2009

(86) PCT No.: PCT/EP2009/054846
§ 371 (c)(1),
(2), (4) Date: May 19, 2011

(87) PCT Pub. No.: WO2009/130256
PCT Pub. Date: Oct. 29, 2009

(65) Prior Publication Data

US 2011/0212118 A1 Sep. 1, 2011
US 2012/0121632 A9 May 17, 2012

Related U.S. Application Data

(60) Provisional application No. 61/046,856, filed on Apr. 22, 2008, provisional application No. 61/053,790, filed on May 16, 2008.

(51) Int. Cl.

| | |
|---|---|
| *A61K 39/21* | (2006.01) |
| *A61K 38/16* | (2006.01) |
| *C07K 14/005* | (2006.01) |
| *A61K 39/00* | (2006.01) |

(52) U.S. Cl.
CPC ............... *A61K 38/162* (2013.01); *A61K 39/21* (2013.01); *C07K 14/005* (2013.01); *A61K 39/00* (2013.01); *A61K 2039/53* (2013.01); *C12N 2740/16322* (2013.01); *C12N 2740/16334* (2013.01)

(58) Field of Classification Search
CPC ... A61K 38/162; A61K 39/21; C07K 14/005; C12N 2740/16334
See application file for complete search history.

(56) References Cited

U.S. PATENT DOCUMENTS

2004/0247614 A1 12/2004 Dorr et al.

FOREIGN PATENT DOCUMENTS

WO WO 00/61067 10/2000

OTHER PUBLICATIONS

Opi, S., et al., 2004, Full-length HIV-1 Tat protein necessary for a vaccine, Vaccine 22:3105-3111.*
Gallo, R. C., Dec. 2005, The end or the beginning of the drive to an HIV-preventive vaccine: a view from over 20 years, The Lancet 366(9500):1894-1898.*
Walker, B. D., and D. R. Burton, May 2008, Toward an AIDS vaccine, 320:760-764.*
Barouch, D. H., Oct. 2008, Challenges in the development of an HIV-1 vaccine, Nature 455:613-619.*
Opi, S., et al., Sep. 2002, Tat HIV-1 primary and tertiary structures critical to immune response against non-homologous variants, J. Biol. Chem. 277(39):35915-35919.*
Watkins et al., "Reservoir Cells No Longer Detectable After a Heterologous SHIV Challenge With Synthetic HIV-1 Tat Oyi Vaccine," Retrovirology Biomed Centeral Ltd. vol. 3, No. 1 p. 8 (2006) XP021019175.
Opi et al., "Tat HIV-1 Primary and Tertiary Structures Critical to Immune Response Against Non-Homologous Variants," Journal of Biological Chemistry, vol. 277, No. 39 (2002) XP002519492.

* cited by examiner

*Primary Examiner* — Jeffrey Parkin
(74) *Attorney, Agent, or Firm* — Cesari and McKenna, LLP

(57) ABSTRACT

The invention relates to a method of preventing or treating acquired immunodeficiency syndrome (AIDS) in a patient, wherein the patient is administered with a Tat protein comprising amino acid sequence SEQ ID NO: 1 or 2, or a variant thereof capable of stimulating an immune response against Tat proteins.

8 Claims, 4 Drawing Sheets

MODIFIED TAT OYI PROTEIN WITH ENHANCED IMMUNOGENICITY

CROSS REFERENCE TO RELATED APPLICATIONS

This application is a National Stage of International Application No. PCT/EP2009/054846, filed on Apr. 22, 2009, which claims the priority of U.S. Provisional Application No. 61/046,856, filed on Apr. 22, 2008 and U.S. Provisional Application No. 61/053,790, filed on May 16, 2008. The contents of the prior applications mentioned above are incorporated herein by reference in its entirety.

The present invention provides compositions and methods for preventing or treating acquired immunodeficiency syndrome (AIDS) in a human patient, and a vaccine against an HIV-infection.

TECHNICAL BACKGROUND

The search for a vaccine against AIDS remains a major issue since the discovery of the HIV-1 (Barre-Sinoussi et al., 1983). The failure of classical vaccine approaches targeting the HIV-1 envelop proteins points out the interest to use another target such as the HIV-1 trans-activator of transcription protein called Tat, due to its extra cellular function involving the collapse of the immune cellular response against HIV infected cells (Jeang et al., 1999).

Tat exists predominantly in two different lengths, 86-87 residues or 99-101 residues, that display multifaceted activities (Jeang et al., 1999). The long forms are predominant in clinical isolates from all HIV-1 subtypes except subtype D, due to the presence of a non-synonymous single nucleotide polymorphism, creating a stop codon in the second exon encoding sequence (Jeang et al., 1999). Tat is divided into six regions (Kuppuswamy et al., 1989) with one called basic region being involved in most of the Tat activities. NMR studies of biologically active Tat variants revealed that the basic region and the other functional regions are well exposed to solvent and surround a core composed of part of the N-terminus with the well conserved Trp 11 (Péloponèse et al., 2000; Gregoire et al., 2001, Watkins et al., 2008). Among different Tat variants this folding is similar in aqueous solution but can change dramatically when exposed to hydrophobic solvent (Péloponèse et al., 1999). Tat is a flexible protein and structural changes are necessary for it to bind to its pharmacological targets (Loret et al., 1992).

Tat is found mainly in the nucleus of infected cells where it functions as a trans-acting transcriptional activator (Wong-Staal et al, 1985; Fujisawa et al., 1985), where it is known to be involved in the initiation of transcription and RNA chain elongation (Cullen, 1990) by a complex process involving interactions with cellular proteins and a stem-bulge loop leader RNA, TAR (trans-activation responsive region), on the viral mRNA and acetylation of the Tat (Bres et al., 2002). Studies have shown that it also participates with the reverse transcription of HIV-1 RNA (Harrich et al., 1997).

Despite the lack of a signal sequence, Tat is the only HIV-1 protein to be secreted by HIV-1-infected cells and is found in detectable levels in the culture supernatants of HIV-1-infected cells (0.1-1 ng/ml) (Ensoli et al., 1990; Westendorp et al., 1995b; Chang et al, 1997) and in the sera of HIV-1-infected patients (1-40 ng/ml) (Xiao et al., 2000; Westendorp et al., 1995b). Extracellular Tat display multifaceted activities (Jeang et al., 1999), but the most important is to trigger apoptosis of uninfected T cells by traversing the cell membrane, leading to apoptosis through the mitochondrial pathway (Chen et al., 2002, Campbell et al., 2004, de Mareuil et al., 2005). Neutralization of extracellular Tat in vivo in SHIV-1 challenged macaques induces a rise of $CD8^+$ T cells and HIV-1 infected $CD4^+$ T cells become undetectable (Watkins et al., 2006).

Thus, the role of Tat in HIV-1 pathogenesis is not only as an essential protein for HIV-1 replication in infected cells, but also as an extracellular toxin (Gallo, 1999). Therefore, it is relevant to develop a vaccine targeting Tat (Goldstein, 1996). However, seropositive patients that have antibodies against Tat are unable to recognize Tat variants from all HIV-1 subtypes (Campbell et al., 2007b). Moreover, these antibodies fail to slow disease progression to AIDS (Senkaali et al., 2008).

It is clear that a Tat vaccine using a B subtype Tat found mainly in Europe and North America as previously proposed (Godstein, 1996, Zagury et al., 1998, Cafaro et al., 1999) has a low probability to provide a therapeutic and a preventive effect against HIV-1 infection in the rest of the world and particularly in Africa. Moreover, a Tat vaccine using a B subtype Tat has also a low probability to provide a therapeutic and a preventive effect even in Europe and North America due to the incapacity of the immune system to neutralize extra cellular Tat.

The two main vaccine strategies against Tat up to now use a short, 86 residue version of a B-subtype European Tat variant that is either inactivated (Zagury et al., 1998) or has full activity (Cafaro et al., 1999). These two approaches were tested on macaques followed by a homologous SHIV-1 challenge (Cafaro et al., 1999; Pauza et al., 2000). A significant decrease of viremia was observed in these two studies carried out respectively on Cynomolgus (Cafaro et al., 1999) and Rhesus macaques (Pauza et al., 2000), without showing complete protection during primo-infection. Another study showed a long term control of infection following SHIV-1 challenge on Tat vaccinated Cynomolgus macaques (Maggiorella et al., 2004). These studies point out that vaccines using biologically active Tat appears to be a safe approach as indicated by safety studies carried out on monkeys in which no local or systemic toxicity or adverse effects were observed (Cafaro et al., 1999, 2001; Caselli et al., 1999, Goldstein et al., 2000).

It is interesting to note that conflicting results appears in Tat vaccine studies on macaques since no protection was observed with a SIV challenge (Allen et al., 2002) or a vaccination with a recombinant virus coding for a Tat-Rev protein (Verrier et al., 2002). These conflicting results could be explained by a different immunization regimens, viral stock, routes of viral challenge and animal species. The difference between SIV Tat and HIV-1 Tat in the first study and the probability that a Tat-Rev recombinant protein does not have the native Tat folding or the native Rev folding for the second study may explain the absence of protection. More puzzling, however, is the result of two other studies using similar viral vectors expressing Tat, Env and Gag that give opposite conclusions. One study shows the efficacy of vectored Tat, but not Gag and Env (Stittelaar et al., 2002), while another study showed efficacy of vectored Gag and Env, but not Tat (Liang et al., 2005). The main difference in the two studies is that one is using a homologous challenge using the Tat Bru sequence in both the vaccine and in the SHIV (Stittelaar et al., 2002) and the other a heterologous challenge with the Tat Bru sequence in the vaccine and Tat Jr in the SHIV (Liang et al., 2005). HIV-1 Jr and HIV-1 Bru are B subtypes (FIG. 1) but their Tat sequences have non-conservative mutations inducing conformational changes (Gregoire & Loret., 1996). Theses mutations between the vaccine and the virus use for the challenge might explain the lack of efficacy of the Tat vectored vaccine in the second study (Liang et al., 2005). It is clear that the second study more closely resembled reality since a vaccinated person will not likely be exposed to a homologous virus infection, but in that case why have homologous Gag and Env been used (Liang et al., 2005)?

Over the last 20 years, HIV-1 vaccine studies that target the HIV-1 envelope proteins have been tested using a homologous SHIV/macaque model and have met with success (Feinberg et al., 2002). However, clinical trials were not successful (Vanichseni et al., 2004). This is due to the high genetic diversity of HIV-1 and this is why heterologous SHIV challenge in macaques, with a genetically distinct virus, should be used to determine if a vaccine can be effective against HIV-1 infection in humans (Feinberg et al., 2002). If a successful homologous SHIV challenge is helpful to show the interest of Tat vaccination in vivo, the development of a Tat vaccine in humans worldwide has to take in account the genetic diversity of Tat. It is important to note that immunization with the B subtype Tat Bru does not stimulate an efficient response against Tat variants from A and C HIV-1 subtypes that corresponds to 75% of the contamination in the world (Opi et al., 2002).

The interest to develop a Tat vaccine rose with the discovery that seropositive long-term non-Progressor (LTNP) patients had a higher level of Tat antibodies than seropositive Rapid Progressor (RP) patients (Re et al., 1995; van Baalen et al., 1997; Zagurry et al., 1998, Re et al., 2001; Addo et al., 2001, Belliard et al., 2003). It is interesting to note that with a serum dilution of 1:1000, Tat Bru is recognized by only 30% of the RP patients in Europe (Zagury et al., 1998) and only 10 to 14% in Africa (Butto et al., 2003). This percentage can reach up to 50% in Africa if other Tat variants from subtypes A, C and D are tested (Campbell et al., 2007). This result outlines again how mutations in Tat variants can affect immunogenicity but it shows also that a large amount of seropositive patients are unable to recognize Tat. Furthermore Tat antibodies in African RP patients have no effect on the progression to AIDS (Sankali et al., 2008). It shows that, for a majority of HIV-1 infected patients, Tat is not recognized while this protein is present in their blood and patients who recognize Tat cannot neutralize this protein. The reason why Tat is so badly recognized by the human immune system could be due to sequence similarity of the basic region of Tat with epitopes found in human proteins such as the protamine. It is clear that triggering an immune response against the Tat basic region (region IV) would lead to autoimmune response on humans. Region IV is well conserved among Tat variants (FIG. 1) but it is not recognized by sera from HIV-1 infected patients (Campbell et al., 2007). It is interesting to note that two third of new born children from HIV-1 infected mother succeed to escape to HIV-1 infection (Beattie et al., 2001). They are seropositive up to 18 months old and then retro seroconvert. This high proportion of new-born infants that resist to HIV infection excludes genetic factors that could be due to an innate immunity against HIV. It could be possible that a repression of the immune system to recognize Tat may exist in adults but not among new-born infants since protamine appears with sexual maturation.

A better attention should be taken to natural immunity occurring in adults against HIV-1. Natural immunity against HIV-1 is observed in a low proportion of the human population and cover different mechanisms going from chemokine mutations to the capacity to produce neutralizing antibodies against HIV-1 envelope (see Marmor et al., 2006 for a review). Natural immunity can be innate or acquired, the latter being of course the most interesting for a vaccine development. Patients with natural immunity against HIV-1 can be exposed and persistently seronegative (EPS) or can be seropositive and long term non progressor (LTNP). In most cases this natural immunity turns out to be an innate immunity. However there is a very rare category of patients highly exposed to the virus that are resistant to HIV-1 due apparently to an acquired immunity. Kenyan sex workers who are EPS had been intensely studied and their resistance to HIV-1 appears to be related to their capacity to develop an efficient CD8 T cell response against HIV-1 (McMichael & Rowland-Jones, 2001). However, the paradox is that the CD8 T cell response in EPS Kenyan sew workers is five time lower in magnitude than that of seropositive Kenyan sex workers who ultimately develop AIDS (Alimonti et al., 2006). To make things even more puzzling, studies of similar cohorts of EPS patients in Ivory Cost, Vietnam and Cambodia show that they have no HIV-1 specific CD8 T cell response but a natural killer (NK) cell responses (Scott-Algara et al., 2003; Jennes et al., 2006), antibodies against HIV-1 envelop proteins (Nguyen et al., 2006) or cellular factors affecting viral entry steps (Saez-Cirion et al., 2006). Although it was believed that these Kenyan EPS patients had an innate immunity, it turned out that it was an acquired immunity at least for some of them who became seropositive after a lapse in sex work (Kaul et al., 2001).

More interesting was the study of an EPS cohort identified in Gabon (Huet et al., 1989). During the eighties in Africa, it was observed in a remote area of Gabon called "Haut Ogooué" that HIV-1 infected patients were not developing AIDS (Delaporte et al., 1988). An epidemiological survey was decided and carried out on 750 pregnant women for two years and 25 were identified as seropositive (Huet et al., 1989). From these 25 seropositive women, 23 retro seroconverted and became EPS during the two years of the survey. Although EPS patients have normally no detectable virus, it was possible to isolate and clone a HIV-1 strain from one patient called Oyi when she was still seropositive (Huet et al., 1989). Contrary to other EPS cohort of sex workers or drug users that were constituted many years after the first exposure to HIV, the Gabon cohort was constituted during the primo infection and explains why it was possible to clone a virus. All women infected with HIV-1 Oyi did retro seroconvert but maintained a CTL response against HIV-1 and had antibodies against P24 (Huet et al., 1989). The high proportion of EPS phenotype in this cohort (92%) indicates that the retro seroconversion was probably due to an acquired immunity and not an innate immunity. Ten years after the publication of this epidemiological survey, the 23 women were in good health and the HIV-1 or a sign of infection was no longer detectable in their blood. Furthermore HIV-1 infection appears to be very low in Gabon compared to other central African countries (Delaporte et al., 1996). HIV-1 Oyi has genes similar to regular HIV-1 strains except the tat gene, which had mutations never found in other Tat variants (Gregoire & Loret, 1996). Immunization with Tat Oyi raises antibodies in rabbits that are able to recognize different Tat variants even with mutations of up to 38%, which is not possible with other Tat variants (Opi et al., 2002). Tat Oyi appears to induce a humoral immune response against a three-dimensional epitope that are conserved in Tat variants and this humoral response could make possible to neutralize extracellular Tat. The role of extracellular Tat was not known during the eighties and the presence of antibodies against Tat was not tested in this Gabon cohort (Huet et al., 1989).

Seven rhesus macaques were immunized with synthetic Tat Oyi complemented with an adjuvant then a heterologous challenge with the European SHIV BX08 was carried out on Tat Oyi vaccinated macaques and control macaques. Tat Oyi vaccinated macaques had a lower viremia associated with a rise of the CD8 T cells compared with control macaques. Moreover, SHIV infected cells were no longer detectable at 8 weeks post-challenge in Tat Oyi vaccinated macaques. It is interesting to note that the macaque that had the lowest viremia had no antibodies against SHIV envelop proteins. The macaque was challenged again, made a short period of seropositivity and seroconverted (Watkins et al., 2006). It was therefore possible to reproduce experimentally on macaque what is observed in the field with EPS patients. It is important to note that this "EPS macaque" had a detectable viremia (watkins et al., 2006). This is a very promising result because it was a heterologous SHIV challenge and it shows that it is possible to dramatically reduce the level of HIV infected cells. This goal has never been achieved in seropositive patients under HAART treatment.

SUMMARY OF THE INVENTION

The invention provides a method of preventing or treating acquired immunodeficiency syndrome (AIDS) in a patient, wherein the patient is administered with a protein comprising amino acid sequence WKHPGSQPKTACNNCYCKRC-CLHCQVCFTKKGLGISYGRKKRRQRRRAPQDSKT HQVSLSKQPASQPRGDPTGPKES (SEQ ID NO:1), or a variant thereof capable of stimulating an immune response against Tat proteins, or a polynucleotide that encodes said protein or variant.

Preferably, the protein or variant is capable of stimulating an immune response against 2, 3, 4 or more HIV-1 subtypes.

In a preferred embodiment, the protein or variant is capable of stimulating an immune response against Tat proteins from two, three, four, five or more HIV-1 subtypes selected from A, B, C, D, E, F, G, H, J, and K.

Most preferably, the protein or variant is capable of stimulating an immune response against five HIV-1 subtypes, preferably A, B, C, D, and E.

Preferably, the protein comprises, or consists of amino acid sequence MEPVDPRLEPWKHPGSQPKTACNNCYCK-RCCLHCQVCFTKKGLGISYGRKKRRQ RRRAPQDSK-THQVSLSKQPASQPRGDPTGPKESKKK-VERETETDPED (SEQ ID NO:2).

Figure 4:
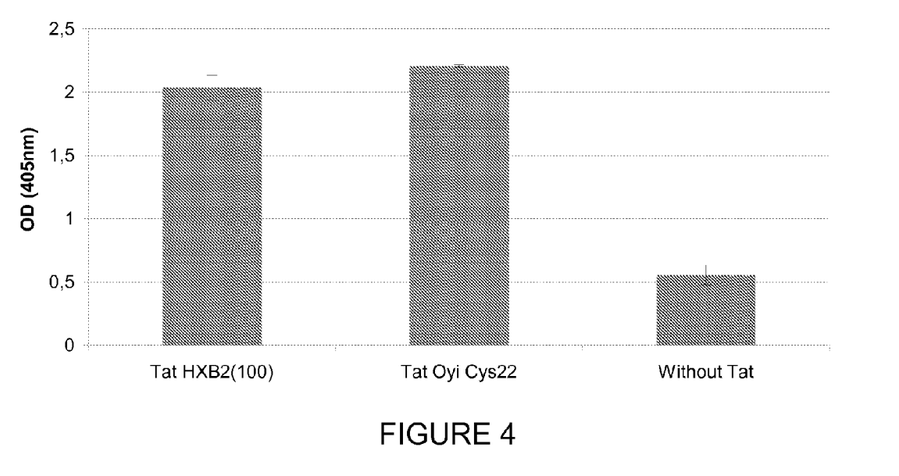

SEQ ID NO:2 differs from HIV Oyi Tat protein described in W000/61067 by a cysteine at position 22, which restores transactivation ability. The protein used herein exhibits the functional activity of Tat, i.e. that is capable of HIV-1 gene transactivation in a HeLa P4 cell assay (FIG. 4).

Figure 2:
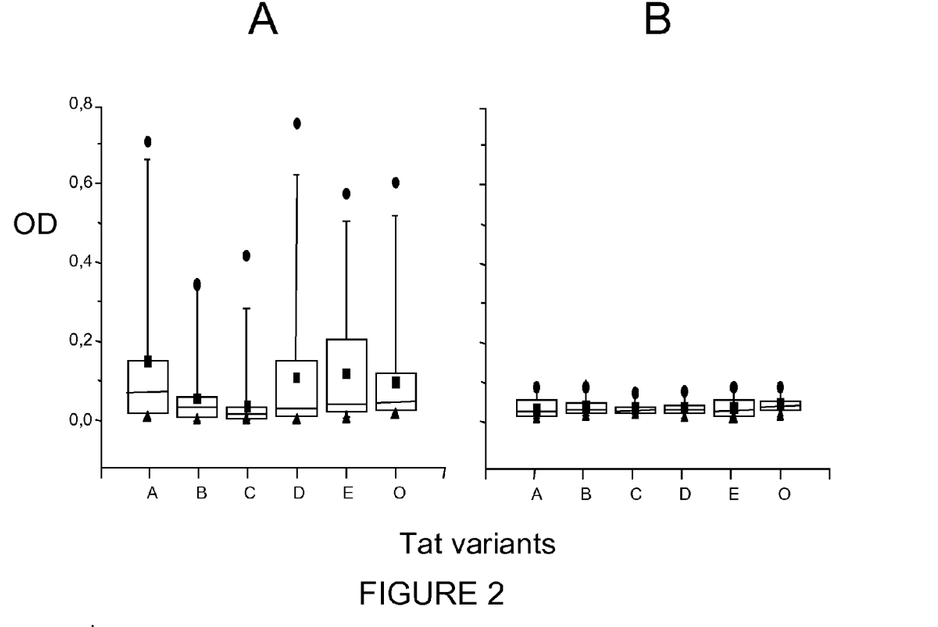

Substituting serine by cysteine at position 22 strengthened immunogenicity of the original Tat Oyi sequence, as shown with sera from a cohort of 100 seropositive patients that recognize better Tat Oyi C22 than Tat Oyi S22 (FIG. 2). The transactivation activity of Tat Oyi Cys 22 confirms that the 3D structure is correct and allows to characterize the protein for a clinical trial.

A further subject of the invention is a vaccine comprising as an active ingredient a transactivation competent Tat Oyi protein comprising a Cysteine at position 22., preferably selected from SEQ ID NO:1 or SEQ ID NO: 2.

In a preferred embodiment, the vaccine comprises an adjuvant.

Still another subject of the invention is a method of immunizing warm-blooded animals comprising injecting an effective amount of a protein comprising at least one of SEQ ID NO:1 or SEQ ID NO: 2 and an adjuvant.

This method may further comprises the step of determining whether the protein triggers an immune response against five or more HIV-1 subtypes, wherein the protein stimulates an immune response against Tat proteins from at least five HIV-1 subtypes.

FIGURE LEGENDS

FIG. 1A shows the recognition of six Tat variants obtained with a serum from a Vietnamese EPS patient. The level of Tat antibodies is not the same regarding the six Tat variants and Tat CM240 was the best recognized for the Vietnamese patients. FIG. 1B shows another patient who recognizes only one or two Tat variants and is mainly observed in the French seropositive cohort (n=100). FIG. 1C is the absence of recognition of any Tat variants (OD inferior to 0.1), and is typical of the French seronegative cohort (n=20), but also half of the French seropositive cohort and a third of Vietnamese EPS cohort.

FIG. 2 is a graph showing recognition of seven Tat variants with sera of the French seropositive cohort (n=100). Tat variant representatives from HIV-1 subtypes A (Ug11RP), B (HXB2), C (96BW), D (Eli) and E (CM240) correspond to the A, B, C, D and E letters. Letter O corresponds to Tat Oyi Ser22 and Oc22 corresponds to Tat Oyi Ser22. This experiment shows that the Cys 22 mutation did not alter the recognition of Tat Oyi but rather strengthened immunogenicity of the original Tat Oyi sequence. This is due certainly to the cystein region that is more similar to Tat wild type.

FIG. 4 is a graph that shows a transactivation assay with HIV LTR Transfected HeLa Cells. The biological activity of the synthetic Tat Oyi Cys 22 was tested with a cellular culture assay using HeLa P4 cells with a bacterial lac-Z gene under the control of the HIV LTR. Active Tat protein can cross cytoplasmic and cellular membranes and "transactivate" the lac Z gene as revealed by the cytoplasmic accumulation of β-galactosidase. $2 \times 10^5$ cells/well were incubated in a 24-well plate at 37° C., 5% CO2, in Dulbecco's modified Eagle's medium (DMEM) supplemented with 10% foetal calf serum. After 24 h, cells were washed with PBS and Tat protein diluted in DMEM supplemented with 0.01% protamine (Sigma), and 0.1% bovine serum albumin (Sigma) was added. One concentration of the two Tat proteins was tested (500 nM) in order to verify that the level of β-galactosidase is dose-dependent regarding extracellular Tat. After 16 h at 37° C., 5% CO2 cells were washed with PBS and lysed. Proteins were extracted, and the β-galactosidase content was measured with a commercial antigen capture enzyme-linked immunosorbent assay (β-galactosidase ELISA, Roche Molecular Biochemicals). Absorbance values were measured at 405 nm.

FIG. 5 shows Circular Dichroism (CD) spectra of Tat Oyi Ser 22 and Tat Oyi Cys 22. CD spectra were recorded at 20° C. in the presence of 20 mM phosphate buffer, pH 4.5, over a 260-178 nm range using a 100 μm path length on a JASCO Corp. J-810 spectropolarimeter (Japan). Data were collected at 0.5 nm intervals using a step auto response procedure (JASCO). CD spectra are presented as Δε per amide. Protein concentration was 1 mg/ml for Tat Oyi Ser22 and 0.3 mg/ml for Tat Oyi Cys22. The two CD spectra are identical and show that the cys22ser mutation does not induce a change that is detectable by CD.

FIG. 6 shows molecular modeling of Tat Oyi Cys22. Molecular modeling was carried out with the Insight II 2002 package including Biopolymer, Discover and Homology (Accelrys, San Diego, Calif.). Two models were built corresponding to Tat Oyi Ser 22 (data not shown) and Tat Oyi Cys 22. The models were obtained from Tat Eli NMR structure (Watkins et al., 2008) using the CV Force Field and gradient conjugate algorithm for energy minimization. The two models were identical and the cys22ser mutation does not induce a change that could be deduced from molecular modeling. It is interesting to observe that the C-terminus containing the Glu 100 mutation is very close of regions 3 and 4 that have the most conserved sequences in Tat variants.

DETAILED DESCRIPTION OF THE INVENTION

The inventor observed that patients that resist to HIV-infection (Vietnamese EPS patients) are able to recognize the Tat variants representative of the five main HIV-1 subtypes (FIG. 1A). These results show that Tat antibodies that have the capacity of cross recognition regarding different Tat variants could restore an efficient cellular immune response against HIV.

On this basis, the invention provides a method of preventing or treating acquired immunodeficiency syndrome (AIDS) in a patient, wherein the patient is administered with a protein comprising amino acid sequence SEQ ID NO:1 or 2, or a variant thereof capable of stimulating an immune response against Tat proteins.

Preferably the protein is capable of stimulating an immune response against two, three, four or more HIV-1 subtypes. Most preferably the protein is capable of stimulating an immune response against Tat variants from at least five HIV-1 subtypes.

In a preferred embodiment, the patient is administered with a protein comprising amino acid sequence SEQ ID NO:2, most preferably a protein consisting of amino acid sequence SEQ ID NO:2.

In another embodiment, the patient is administered with a protein comprising a truncated form of sequence SEQ ID NO: 1 or 2. For instance, the protein may be truncated of 1 to 10 amino acids, preferably 1 to 8, preferably 1 to 6, preferably 1 to 4, preferably 1 or 2 amino acids at the N-terminus. The patient may also administered with a protein comprising amino acid sequence SEQ ID NO:1 or 2 truncated of 1 to 14 amino acids, preferably 1 to 12, preferably 1 to 10, preferably 1 to 8, preferably 1 to 6, preferably 1 to 4, preferably 1 or 2 amino acids at the C-terminus.

The protein to administer may be a variant deriving from SEQ ID NO:1 or SEQ ID NO:2.

Preferably, the protein variant differs from SEQ ID NO:1 or SEQ ID NO:2 by conservative amino acid substitutions. Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Preferably the protein variant, capable of stimulating an immune response against Tat proteins, preferably from at least five HIV-1 subtypes, shows at least 80%, preferably at least 85%, preferably at least 90%, preferably at least 95% identity with SEQ ID NO:1 or SEQ ID NO:2.

Homology or identity is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology or identity is established by recording all of the positions in which the amino acids of both sequences are identical, relative to the total number of positions.

The protein variant to administer may also comprise chemical modifications, e.g. modification of peptide bonds into a pseudopeptide bond.

The term "pseudopeptide" refers to compounds that are similar to the reference peptide but in which one or more peptide bonds —CO—NH— are substituted by a bond that is equivalent to the peptide bond, called a pseudopeptide, such as —CH2-NH—, —CH2-S—, —CH2-O—, —CO—CH2-CO—, —CH2-CH2—for example.

The term "variant" further encompasses substitution of one or several amino acids by a chemical residue which is not a natural amino acid. Substitutions by L-amino acids is also included.

In another aspect of the invention, the protein is covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, the protein half-life is increased by including the protein in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

In still a further embodiment, the protein is bound to, or is associated with, a carrier. Carriers are known in the art (Plotkin, 1999). Bacterial carriers (i.e., carriers derived from bacteria) include, but are not limited to, cholera toxin B subunit (CTB); diphtheria toxin mutant (CRM197); diphtheria toxoid; group B streptoccus alpha C protein; meningococcal outer membrane protein (OMPC); tetanus toxoid; outer membrane protein of nontypeable Haemophilus influenza (such as P6); recombinant class 3 porin (rPorB) of group B meningococci; heat-killed *Brucella abortus*; heat-killed *Listeria monocytogenes*; and *Pseudomonas aeruginosa* recombinant exoprotein A. Another carrier is keyhole limpet hemocyanin (KLH). Examples of viral-derived carriers are known in the art and include hepatitis B surface antigen (HBsAg) particles and hepatitis B core antigen (HBcAg).

In a preferred embodiment, the protein variant, capable of stimulating an immune response against Tat proteins, preferably from at least five HIV-1 subtypes, is capable of transactivation.

Advantageously the protein variant is capable of stimulating an immune response against Tat proteins from HIV-1 subtypes A, B, C, D, and E (E subtype HIV strains are observed mainly in South East Asia but are often considered as recombinant forms of A subtype strains).

The protein or variant may be a recombinant protein, or preferably a chemically synthesized protein, that may be synthesized in a solid phase synthesis and preferably fast FMOC strategy.

When the protein is produced by chemical synthesis, the polypeptide according to the invention may be synthesized in the form of a single sequence, or in the form of several sequences which are then linked to one another. The chemical synthesis may be carried out in solid phase or in solution, these two synthesis techniques being well known to those skilled in the art. These techniques are in particular described by Atherton and Shepard in "Solid phase peptide synthesis (IRL press Oxford, 1989) and by Houbenweyl in "Methoden der organischen Chemie" [Methods in Organic Chemistry] published by E. Wunsch Vol. 15-I and II, Stuttgart, 1974, and also in the following articles, which are entirely incorporated herein by way of reference: P E Dawson et al. (Science 1994; 266(5186):776-9); G G Kochendoerfer et al. (1999; 3(6):665-71); et P E Dawson et al., Annu Rev. Biochem. 2000; 69:923-60.

The protein may also be produced using genetic engineering techniques well known to those skilled in the art. When the protein is produced by genetic engineering, it comprises, at the NH 2-terminal end, an additional methionine residue corresponding to the translation of the first initiation codon. These techniques are described in detail in Molecular Cloning: a molecular manual, by Maniatis et al., Cold Spring Harbor, 1989.

The protein may thus be obtained in purified form, i.e. in a form exhibiting a degree of purity of at least 80%, 85%, 90%, 95%, or greater. The degree of purity is defined relative to the other proteins present in the mixture which are considered to be contaminants. This degree is evaluated by colorimetry of an SDS-PAGE using coomassie blue. Densitometric measurement of the bands makes it possible to quantify the degree of purity. The degree of purity may also be measured by reverse-phase HPLC, by measuring the area of the various peaks.

Several types of therapeutic compositions can be used to elicit an immune response against Tat proteins from at least five HIV-1 subtypes.

A subject of the invention is a pharmaceutical composition comprising a protein comprising amino acid sequence SEQ ID NO:1 or SEQ ID NO:2, or a variant thereof capable of stimulating an immune response against Tat proteins, preferably from at least five HIV-1 subtypes, in combination with a pharmaceutically acceptable carrier.

Immunogenic compositions, proposed to be suitable for use as a vaccine, may be prepared most readily directly from immunogenic Tat Oyi Cys 22 proteins and/or peptides (e.g., SEQ ID NO.:1, 2, or fragments of SEQ ID NO.:1 or 2) prepared in a manner disclosed herein. Preferably, the antigenic material is extensively dialyzed to remove undesired small molecular weight molecules and/or lyophilized for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770. Typically, such vaccines are prepared as injectables: either as liquid solutions or suspensions, solid forms suitable for solution in, or suspension in, liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10-95% of active ingredient, preferably 25-70%.

The proteins may be formulated into the vaccine as neutral or salt forms. Pharmaceutically acceptable salts, include acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

In a preferred embodiment, the composition of the invention further comprises an adjuvant. The adjuvant may be selected from any substance, mixture, solute or composition facilitating or increasing the immunogenicity of the protein which comprises amino acid sequence SEQ ID NO:1 or SEQ ID NO:2, or its variants, wherein the adjuvant is able to enhance an immune response. Examples of adjuvants include preferentially calcium phosphate but also ALUM phosphate, ALUM hydroxide, Montanide CpG, QS21, ISCOM or monophosphoryl lipid A.

Other methods of achieving adjuvant effect for the vaccine include use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the antigens.

The protein composition according to the present invention may be prepared using any conventional method known to those skilled in the art. Conventionally, the protein is mixed with a pharmaceutically acceptable diluent or excipient, such as water or phosphate buffered saline solution. The excipient or diluent will be selected as a function of the pharmaceutical form chosen, of the method and route of administration, and also of pharmaceutical practice. Suitable excipients or diluents, and also the requirements in terms of pharmaceutical formulation, are described in detail in Remington's Pharmaceutical Sciences, which represents a reference work in this field.

Another pharmaceutical composition comprises a polynucleotide that encodes amino acid sequence SEQ ID NO:1 or SEQ ID NO:2, or a variant thereof as defined above. Such pharmaceutical composition is administered to a host, for instance injected (known as DNA vaccination) and said nucleic acid expresses in vivo the Tat polypeptide. Such DNA vaccines usually consist of plasmid vectors. The delivery of naked DNA has shown to be poorly efficient, and some carriers are usually needed to improve the delivery and uptake of DNA into cells. Two types of carriers have been yet developed: (1) viral carriers (adenoviruses, lentiviruses, measles virus), or (2) non-viral carriers such as polymers (and especially cationic polymers), encapsulated-DNA (liposomes, comprising cationic lipids interact spontaneously and rapidly with polyanions, such as DNA and RNA, resulting in liposome/nucleic acid complexes) or DNA linked to gold microparticles. Moreover, agents, which assist in the cellular uptake of nucleic acid, such as calcium ions, bacterial proteins, viral proteins and other transfection facilitating agents, may advantageously be used.

The compositions mentioned above may be administered via any conventional route usually used in the field of vaccines, such as the parenteral (intravenous, intramuscular, subcutaneous, etc.) route. In the context of the present invention, intramuscular administration will preferably be used for the injectable compositions. Such an administration may advantageously take place in the thigh or arm muscles. The compositions according to the present invention may also advantageously be administered orally. Administration via the nasal, vaginal or rectal mucosa may also be recommended in the context of the present invention. The administration may also be carried out by giving a single dose or repeated doses, for example on D0 and at 1 month, 3 months, 6 months and 12 months. Injections at J0 and at 1 month and 3 months, with a booster, the periodicity of which may easily be determined by the treating physician, will preferably be used.

Generally, each dose will comprise between about 5 µg to about 500 µg of the protein, preferably between 10 to 200 µg. A more preferred dosage may be about 50 µg of the protein as immunogen. Other dosage ranges may also be contemplated by one of skill in the art. Initial doses may be optionally followed by repeated boosts, where desirable.

The present invention is also intended to cover the pharmaceutical compositions for use as a medicinal product, in particular for use as a prophylactic or therapeutic vaccine against HIV infection.

According to a preferred aspect, a subject of the present invention is the use of a protein as described herein, or a polynucleotide that encodes said protein, for immunizing the human body. The present invention therefore preferably relates to a method for administering said polypeptide or polynucleotide so as to induce a specific humoral response.

The present invention thus provides a method for inducing HIV neutralizing antibodies comprising administration of a quantity of a pharmaceutical composition as defined above which is sufficient to induce the said humoral response.

The expression "a specific humoral response" is intended to mean a response comprising the production of antibodies directed specifically against a surface well conserved among Tat variants. The production of specific antibodies may be easily determined using conventional techniques well known to those skilled in the art, such as ELISA, RIA or western blot.

The Tat protein and variant used herein are candidates of value for developing a vaccine which can be used for the protection and/or treatment of a large number, or even all, of the individuals at risk from or infected with HIV.

A therapeutic effect is recognized if seropositive patients that have no antiviral treatment have a lower viremia, a rise of lymphocyte CD4 cells and/or a lower content in lymphocyte CD8 cells.

More particularly, a therapeutic effect is recognized when 30% of a cohort of at least 55 HIV seropositive patients maintain their viremia under 50 copies/ml after interruption of their HAART treatment for six months.

In patients with declared AIDS, such anti-Tat vaccine could limit the incidence of certain pathological conditions such as Kaposi's sarcoma or neurological syndromes which appear to be linked to a direct action of the Tat protein following their secretion by HIV-infected cells.

In asymptomatic patients, the pharmaceutical composition of the invention is expected to delay the progression toward AIDS due to a lower viremia, a rise of lymphocyte CD4 cells and/or a lower content in lymphocyte CD8 cells. Such a vaccine would allow the patient to restore an efficient immune cellular response against HIV infected cells, as appears to be not the case at the onset of the infection. In particular, the restoration of the activity of the cytotoxic T lymphocytes (CTL), NK cells and macrophages, but whose activity is inhibited by Tat. The vaccination would have the consequence of allowing the patients to become at least non progressors. It is herein provided a vaccination for eliminating HIV infected cells and providing a curative treatment against AIDS.

The figures and examples illustrate the invention without limiting its scope.

EXAMPLES

Materials and Methods

Protein Synthesis.

The Tat proteins were assembled according to the method of Barany and Merrifield (1980) on HMP preloaded resin (0.5-0.65 mmol) (Perkin Elmer, Applied Biosystem Inc., Forster City, Calif.) on an automated synthesiser (ABI 433A, Perkin Elmer, Applied Biosystem Inc.)

Transactivation Assay with HIV LTR Transfected HeLa Cells.

The biological activity of the synthetic Tat Oyi Cer22 was tested with a cellular culture assay using HeLa P4 cells with a bacterial lac-Z gene under the control of the HIV LTR. Active Tat protein can cross cytoplasmic and cellular membranes and "transactivate" the lac Z gene as revealed by the cytoplasmic accumulation of β-galactosidase. $2 \times 10^5$ cells/well were incubated in a 24-well plate at 37° C., 5% CO2, in Dulbecco's modified Eagle's medium (DMEM) supplemented with 10% foetal calf serum. After 24 h, cells were washed with PBS and Tat protein diluted in DMEM supplemented with 0.01% protamine (Sigma), and 0.1% bovine serum albumin (Sigma) was added. One concentration of the two Tat proteins were tested (500 nM) in order to verify that the level of β-galactosidase is dose-dependent regarding extracellular Tat. After 16 h at 37° C., 5% CO2 cells were washed with PBS and lysed. Proteins were extracted, and the β-galactosidase content was measured with a commercial antigen capture enzyme-linked immunosorbent assay (β-galactosidase ELISA, Roche Molecular Biochemicals). Absorbance values were measured at 405 nm.

Circular Dichroism (CD)

CD spectra were recorded at 20° C. in the presence of 20 mM phosphate buffer, pH 4.5, over a 260-178 nm range using a 100 μm path length on a JASCO Corp. J-810 spectropolarimeter (Japan). Data were collected at 0.5 nm intervals using a step auto response procedure (JASCO). CD spectra are presented as Δε per amide.

Molecular Modeling:

Molecular modeling was carried out with the Insight II 2002 package including Biopolymer, Discover and Homology (Accelrys, San Diego, Calif.). The models were obtained from Tat Eli NMR structure (Watkins et al., 2008) using the CV Force Field and gradient conjugate algorithm for energy minimization.

Human Sera.

The exposed persistently seronegative (EPS) patients (n=25) were Vietnamese intravenous drug users (IDU) who had been highly exposed to the risk of HIV-1 infection through needle sharing and followed since 1996 (Truong et al, 2003) and gave their agreement for scientific studies (Tran et al, 2006). French human blood samples were obtained from a group of 20 HIV-1 seronegative and 100 HIV-1 seropositive Caucasian patients. They were collected in hospital centers in Marseille. Most of the HIV-1 seropositive patients are under antiretroviral therapy (HAART). Enrolled participants in the French seronegative cohort were informed of the purpose of the study (in accordance with the Helsinki Declaration of 1975 and revised in 1983). All blood samples were collected and frozen in the country of origin of each population.

ELISA Assay.

Antibodies against that in human or mice sera were detected by standard Enzyme Linked Immunosorbent Assay (ELISA) using Maxisorp U96 immunoplates (Nunc). Plates were coated for 16 h at 4° C. with 0.5 μg/well for each Tat variants diluted in phosphate buffer 100 mM pH 4.5. Currently, there are five main HIV-1 subtypes in the world: subtypes A and C are predominant (72%) and are found mainly in Africa, India and South America; subtype B (10%) is mainly found in Europe and North-America; subtype D is found mainly in Africa and subtype E (now described as the recombinant form CRF_01AE) is found mainly in South East Asia (Hemelaar et al., 2006). Tat variability follows this geographical diversity with mutations of up to 40% observed among Tat variants from A, B, C, D and E HIV-1 subtypes, that do not modify Tat activity but affect Tat immune properties (Opi et al., 2002, 2004). This is why we used Tat Ug 11 RP, Tat HXB2, Tat 92Br, Tat Eli and Tat CM240 to represent HIV-1 subtypes A, B, C, D and E. These five synthetic proteins have the Tat biological activity and a size going from 99 to 101 residues which is now the dominant form of Tat in the field (Jeang et al., 1999). The recognition of Tat Oyi Cys 22 and Tat Oyi Ser 22 was compared on a same plate with these five Tat variants Plates were then incubated for 1 h at RT with 200 μl of PBS supplemented with 2% milk. Sera (one serum for one plate) were added in different dilutions of PBS supplemented with 0.2% milk and shacked gently for 1 h at RT. Secondary antibody (anti-Human or anti mice IgG peroxidase from Sigma) diluted 1:1000 in PBS supplemented with 0.2% milk was added to each well and shacked gently for 1 h at RT. Plates were washed 3× with 200 μl of 1× PBS/0.05% Tween 20 (Genaxis) between each subsequent step. Revelation was carried out with 100 μl of ABTS (2,2'-azino-bis-3-ethylbenz-thiazoline-6-sulfonic acid from Sigma) added to each well and absorbance was read in an EL800 universal microplate reader (BIO-TEK INSTRUMENT, INC) at 405 nm.

Example 1

Figure 1:
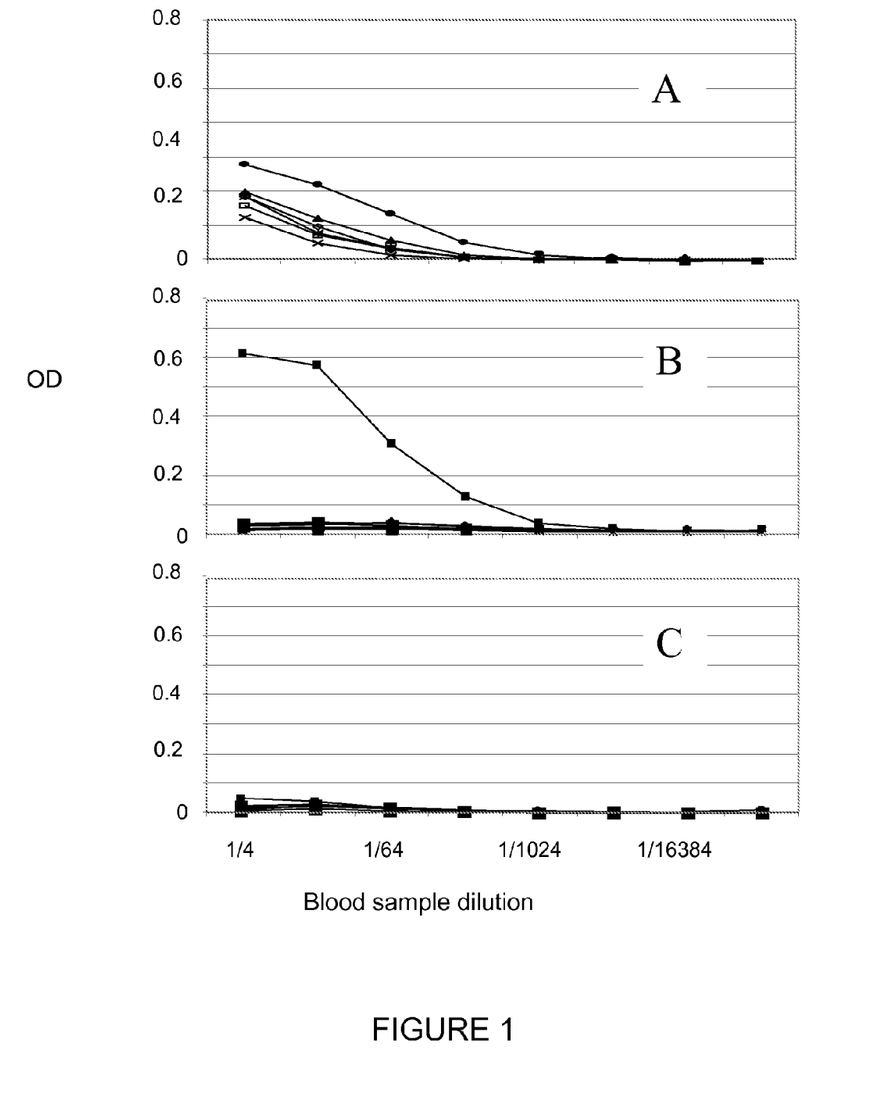
FIG. 1 is a graph showing detection of Anti-Tat IgG in three cohorts, one was Vietnamese EPS patients (n=25), the second was French seropositive patients (n=100) and the third was French seronegative naive patients (n=20). Three types of serological pattern were observed with patients blood samples in the ELISA titration curves with Tat variants representative of the five main HIV-1 subtypes.

Sera from Vietnamese EPS Patients can Recognize Tat Variants from the Five Main HIV-1 Subtypes including Tat Oyi Anti-Tat IgG Detected in EPS Patients:

We were able to detect Tat antibodies in a cohort of EPS patients in Vietnam. We carried out ELISA test with Tat variants representative of the five main HIV-1 subtypes including Tat Oyi on three cohorts, one was Vietnamese EPS patients (n=25), the second was French seropositive patients (n=100) and the third was French seronegative naive patients (n=20). Three types of serological pattern were observed in Elisa test (FIG. 1). The first one is characterized by the specific recognition (OD superior to 0.1) of all Tat variants and is observed only in the EPS cohort (n=25). FIG. 1A shows the recognition of six Tat variants obtained with a plasma from a Vietnamese EPS patient. The level of Tat antibodies is not the same regarding the six Tat variants and Tat from HIV-1 CM240 (Can et al., 1996) is best recognized for this patient. The second serological pattern is characterized by the absence of specific recognition for at least one Tat variant and is mainly observed in the seropositive cohort (n=100). FIG. 1B shows the recognition of only one Tat variant obtained with a serum from a French seropositive patient. Seropositive patients can recognize more than one Tat variant but can not recognize all Tat variants (Campbell et al., 2007). The third serological pattern is the no recognition of any Tat variants, which is characterized by an OD inferior to 0.1. FIG. 1C show no recognition of Tat variants obtained with a serum from a French seronegative patient. This serological pattern is observed in all volunteers of the French seronegative cohorts of naive patients, but also in half of the French seropositive patients, and in a third of the Vietnamese EPS cohort (data not shown). It is interesting to note that Tat CM240 is the best recognized in the Vietnamese cohort followed by Tat Oyi as shown in FIG. 1A. Tat CM240 is representative of HIV-1 E subtype that is endemic in Vietnam (Lan et al., 2003). The good recognition of Tat Oyi in these Vietnamese patients shows the specific immune characteristic of Tat Oyi.

No Cross Recognition of the Six Tat Variants Observed in Seropositive Patients:

The main difference with EPS patients is shown in FIG. 1B. Only half of the patients had Tat antibodies and their sera were generally able to recognize one or two Tat variants (FIG. 1B). This result is very similar to what was observed with a Uganda cohort of seropositive patients (Campbell et al., 2007). However the design of this study was different since five blood sampling was made for one year in the French seropositive cohort. It was very interesting to note that antibodies against Tat could disappear in some patients and when they have again antibodies against Tat, it is the same Tat variant that is recognized (data not published). Most of the French seropositive patients (75%) were infected by B subtype HIV-1 strain and 75% recognize effectively Tat HXB2, Tat Oyi Ser 22 or Tat Oyi Cys 22. However it is interesting to observe that Tat Oyi is better recognized than Tat HXB2, although the Tat HXB2 sequence has the closest homology with European B-subtype Tat variants. As for the EPS Vietnamese cohort, these results confirm the specific immune characteristic of Tat Oyi.

We expected that the Ser/cys 22 mutation would not alter the immune recognition of Tat Oyi. This was confirmed by the French seronegative cohort since the Cys 22 mutation did not alter the recognition of Tat Oyi. It is interesting to observe that the recognition of Tat Oyi Cys 22 is even better compared to Tat Oyi S22 due probably to the homology of the cysteine rich region with wild type Tat variants.

Titration curves are often identical for Tat Ug 11RP and Tat CM240 in the French seropositive cohorts (data not shown). This suggests that a similar epitope is recognized in these two variants and increase artificially the number of patients recognizing these two variants. Titration curves are different for Tat Ug 11RP and Tat CM240 in Vietnamese EPS patients as illustrated in FIG. 1A where the top curve is due to Tat CM240. This indicate that it exists another epitope common to Tat CM240 and E subtype Tat variants in Vietnam. Titration curves are also often identical between Tat Oyi and Tat HXB2 both for Vietnamese and French patients (data not shown).

FIG. 1 and FIG. 2 show that there is not a common epitope among Tat variants since our Elisa test allows almost to identify the HIV-1 subtype that infected the patients. Consequently, it makes very improbable the possibility that the detection of Tat IgG antibodies in EPS patients could be due to the infection from a pathogen that would not be HIV-1.

Discussion

Tat Oyi (101 residues) has mutations never found in Tat variants from patients that are rapid progressors (Gregoire & Loret, 1996), and we assume that these mutations give to Tat Oyi the capacity to have a 3D epitope corresponding to a well conserved region in Tat variants (Opi et al., 2002, Watkins et al., 2006). It is therefore surprising that Tat Oyi is very well recognized in the Vietnamese EPS cohort and this recognition cannot be explained by a common epitope with Tat HXB2.

This study reveals that Tat from HIV-1 CM240 identified in a Thai patient (Carr et al., 1996) is the most recognized in Vietnamese EPS patients. HIV-1 CM240 is typical of South-East Asia and this result indicates that an acquired humoral response against Tat probably occurred in EPS and could be the cause of their resistance to HIV-1 in spite of multiple exposure. A specific humoral response was also observed in this EPS Vietnamese cohort regarding CD4-GP120 complex (Lopalco et al., 2005). This EPS Vietnamese cohort has similar signs of HIV-1 immunity regarding an EPS cohort of European patients (Lopalco et al., 2005), and the recognition of Tat CM240 confirms that the EPS Vietnamese patients were HIV infected and successfully resisted to HIV-1 infection. On the other hand, it appears that a third of the EPS patients have no Tat antibodies detectable and their resistance to HIV is not due to Tat antibodies (data not shown) Innate immunity was recently identified in this very same Vietnamese EPS cohorts, where five patients had mutations in their CD4 lymphocytes cellular factors affecting HIV entry steps (Saez-Cirion et al., 2006). It is interesting to know that one of these patients is among the EPS patients that do not recognize Tat in this study.

Tat antibodies have been detected in sera of seropositive patients and a correlation was observed with the long term non progressor (LTNP) status (Zagury et al., 1998; Re et al., 2001; Belliard et al., 2003). Denatured Tat variants or peptides were used in these studies and Tat antibodies was detected only in a third of the seropositive patients (Zagury et al., 1998). We developed a new protocol to detect Tat antibodies in using full Tat variants at pH 4.5 to maintain the three dimensional structure of Tat and in starting the detection at low dilution (¼) of blood samples. This new protocol makes possible to increase the detection of specific Tat antibodies to 50% of seropositive patients. It is however amazing that 50% of seropositive patients that have extra cellular Tat in their blood do not recognize any Tat variants. In the other hand, although the concentration of Tat antibodies is twice higher in seropositive patients regarding EPS patient, the amount of Tat antibodies remains huge in EPS patients regarding the potential amount of HIV infected cells producing Tat. What is odd in the Vietnamese is the recognition of Tat Oyi. In a first screening experiment with the Vietnamese cohorts using a ¹⁄₁₀₀₀ blood sample dilution, we were able to detect the presence of antibodies against Tat Oyi in 56% of the EPS patients. The new protocol starting with ¼ blood sample dilution made it possible to point out that other Tat variants were significantly recognized in the EPS cohort (FIG. 1A).

Conclusion:

Only half of the seropositive patients have antibodies against Tat and cannot recognized the six Tat variants. Moreover, these antibodies against Tat can disappear. These characteristics might explain their incapacity to neutralize extra cellular Tat. It was shown that Tat can induce apoptosis in cytotoxic T lymphocytes (Westendorp et al., 1995) and inhibit macrophages due to the over expression of Fas ligand (Cohen et al., 1999). The only cellular response against HIV-1 in the EPS cohort was due to natural killer (NK) cells and Tat can induce cellular apoptosis in NK cells (Poggi et al., 2002). Our results suggest that Tat antibodies that have the capacity of cross recognition regarding different Tat variants could restore an efficient cellular immune response against HIV. The presence of IgG recognizing specifically Tat among a majority of patients in the EPS cohort suggests that an acquired immunity against Tat did occur and made possible a recovery of their cellular immunity. This acquired immunity could be due to mutations in a Vietnamese Tat variant similar to mutations observed in Gabon with Tat Oyi. Among the mutations that are specific of Tat Oyi, Glu 100 appears to be very interesting because the apparition of a negative charge could induce an immogenicity to a surface of Tat Oyi corresponding to a highly conserved surface among Tat variants.

Example 2

Synthesis, Purification and Characterization of Tat Oyi Cys 22

Tat OyiCys22 (SEQ ID NO:2) was assembled in solid-phase peptide synthesis. Before cleavage of the resin, 330 mg of crude material were obtained from a theoretical amount of 707 mg. The synthesis yield was 46.7% and is similar to the one observed with the synthesis Tat Oyi Ser 22.

Resin and protecting groups were cleaved from the protein content with acid trifluroacetic. The protein content was first purified by a precipitation with tertio buthyl Ether (TBE) to remove the free protecting groups that are soluble in TBE. The pullet was dried and re-suspended in a 0.1% TFA water buffer and then the resin was remove by filtration (0.22 µm). The resin-free protein content (approximately 240 mg) was freeze dried and re-suspended in 0.1% TFA water buffer at concentration up to 20 mg/ml in four fractions of approximately 60 mg called F1, F2, F3 and F4. Each fraction containing around 15 OD units.

Purification was carried out on each fraction using a Beckman high-pressure liquid chromatography (HPLC) apparatus with a Beckman C8 reverse phase column (10×150 mm). Buffer A was water with 0.1% TFA and buffer B was acetonitril (Merck) with 0.1% TFA. Gradient was buffer B from 15-35% in 40 minutes with a 2 ml/min flow rate.

From the different sub-fractions obtained after C8 reverse phase separation, it was possible to detect the typical absorption spectrum of Trp in sub-fractions. HPLC analysis was carried out with a Merck RP-8 column (4.6×100 mm) with similar buffers but using a gradient from 10-50% in 40 minutes with a 0.8 ml per minute flow rate. The subfraction having the typical absorption spectrum of Tip was characterized by a single peak at 25 min that has the same retention time that Tat Oyi Ser 22 (data not shown). The mutation did not change the hydrophobicity of Tat Oyi.

Figure 3:
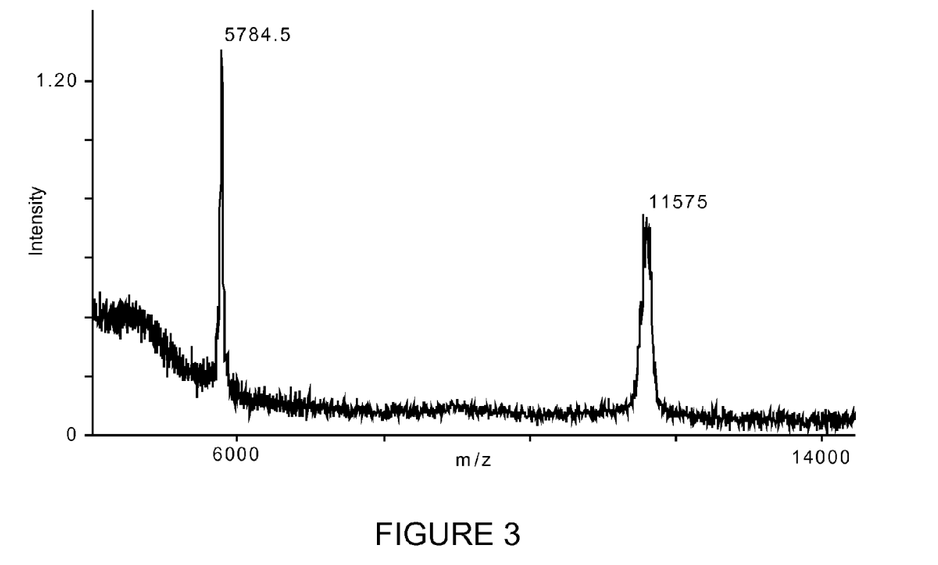
FIG. 3 shows a mass spectroscopy of an aliquot from a purified sub fraction having a single peak at 25 min in analytical HPLC. The molecular weight (MW) observed corresponds almost exactly to the MW expected of 11578 for Tat Oyi Cys 22. Purification was successful with no trace of peptides with a molecular weight inferior or superior to 11578. The peak at 5784.5 corresponds to the shadow peak (mass divided by two) of the peak at 11575.

A mass corresponding to the expected 11578 MW of Tat Oyi Cys 22 was observed with the sub fraction that has a single peak at 25 min in HPLC (FIG. 3). No contaminant was observed by mass spectroscopy. It is interesting to note that the same mass spectrum was obtained after six month with Tat Oyi Cys22 stored at −22° C. The absence of degradation of the active principle is encouraging for a vaccination campaign.

The total amount of purified Tat Oyi Cys 22 corresponds to a third of OD units at 280 nm and ⅕ of the total amount of protein content.

Figure 5:
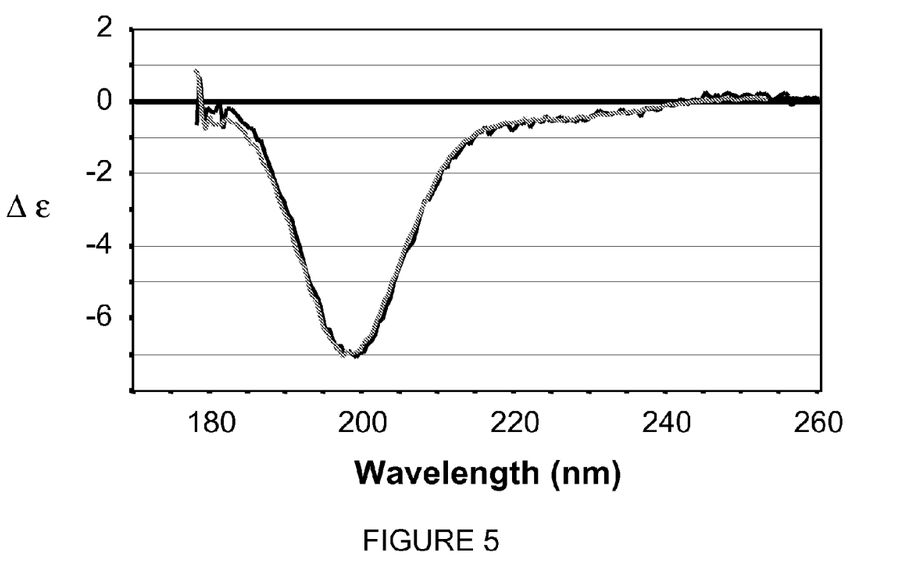

Further characterization such as transactivation assay (FIG. 4) and circular dichroism (FIG. 5) was carried out with Tat Oyi Cys 22. Transactivation assays was carried out with Tat HXB2 as a control. Transactivation was observed with Tat Oyi Cys 22 with a level similar to Tat HXB2, while the variant Tat Oyi Ser 22 is unable to transactivate. The Cys 22 mutation makes possible to have a biological test showing that Tat Oyi Cys 22 has a structure similar to other active Tat variants.

Circular dichroism (CD) was carried out on Tat Oyi Cys 22 and Tat Oyi Ser 22 the same day. CD spectra (FIG. 5) reveals that the mutation Cys22Ser does not induce a structural change detectable with CD.

Figure 6:
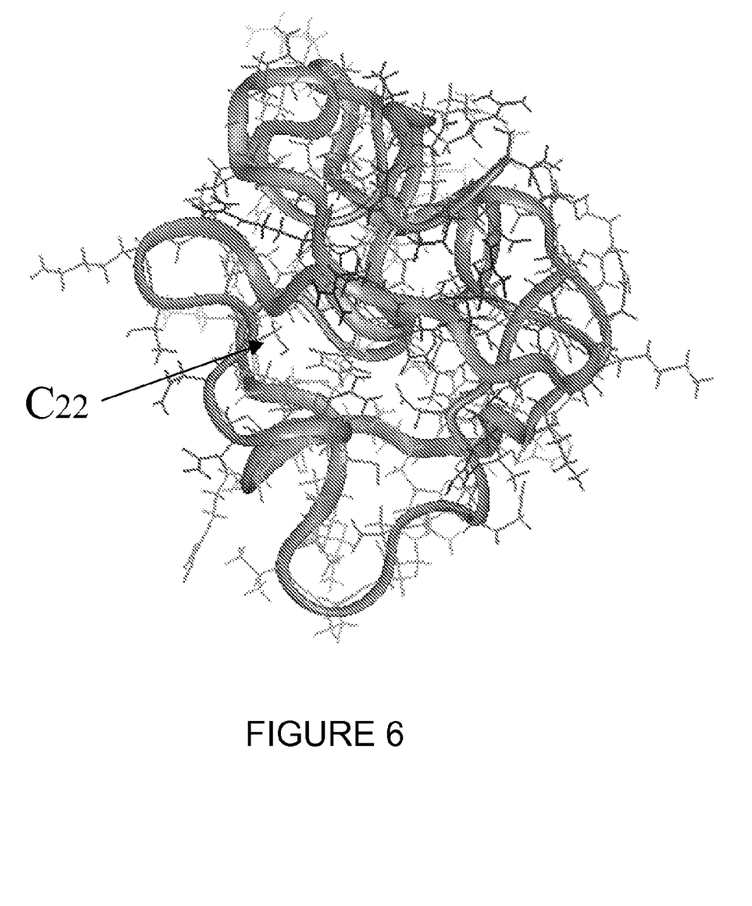

To evaluate a potential change that could be induced by the mutation but not detected with CD, a molecular modeling of the Tat Oyi Cys22 and Tat Oyi Ser22 was carried out (FIG. 6). Molecular modeling confirms that the mutation Ser22Cys does not induce a structural change. The only difference between Ser and Cys is a different atom (oxygen instead of a sulfur) in the lateral chain. Sulfur and oxygen are on the same column of the Mendelief table and share chemical similarity as nucleophil. Sulfur is bigger than oxygen and the hydrogen linked to sulfur is more labile than the one linked to oxygen. That seems to be the only explanation why Tat OyiCys22 is able to transactivate and not Tat OyiSer22.

It is interesting to observe that the C-terminus containing the Glu 100 mutation is very close of regions 3 and 4 that have the most conserved sequences in Tat variants.

Example 3

Immunization with Tat Oyi Cys 22

Immunization of Mice was carried out with Tat Oyi Cys 22 (SEQ ID NO:2). No toxicity was observed on mice with Tat Oyi Cys 22 concentration that is 1000 fold higher compared to what is planned for clinical trials (data not shown).

REFERENCES

Addo M M, Altfeld M, Rosenberg E S, Eldridge R L, Philips M N, Habeeb K, Khatri A, Brander C, Robbins G K, Mazzara G P, Goulder P J, Walker B D; and HIV Controller Study group: The HIV-1 regulatory proteins Tat and Rev are frequently targeted by cytotoxic T lymphocytes derived from HIV-1-infected individuals. *Proc Natl Acad Sci USA* 2001, 98, 1781-1786.

Alimonti, J. B., Kimani, J., Matu, L., Wachihi, C., Kaul, R., Plummer, F. A., & Fowke, K. R. Characterization of CD8 T-cell responses in HIV-1-exposed seronegative commercial sex workers from Nairobi, Kenya. *Immunol Cell Biol.* 2006, 84:482-485.

Allen, T. M., L. Mortara, B. R. Mothe, M. Liebl, P. Jing, B. Calore, M. Piekarczyk, R. Ruddersdorf, D. H. O'Connor, X. Wang, C. Wang, D. B. Allison, J. D. Altman, A. Sette, R. C. Desrosiers, G. Sutter, and D. I. Watkins. Tat-vaccinated macaques do not control simian immunodeficiency virus SIVmac239 replication. *J. Virol.* 2002, 76: 4108-4112.

Arya S K, Guo C, Josephs S F, Wong-Staal F: Trans-activator gene of human T-lymphotropic virus type III (HTLV-III) *Science* 1985, 229:69-73.

Barany, G. & Merrifield, R. B. The peptide: Analysis, Synthesis, Biology. Volume 2. Edited by: Gross E, Meinhofer J. Academic Press, New York, 1980:1-284.

Barre-Sinoussi F, Chermann J C, Rey F, Nugeyre M T, Chamaret S, Gruest J, Dauguet C, Axler-Blin C, Vezinet-Brun F, Rouzioux C, Rozenbaum W, Montagnier L. Isolation of a T-lymphotropic retrovirus from a patient at risk for acquired immune deficiency syndrome (AIDS). 1983. *Science.* 1983, 220:868-871.

Bell C M, Connell B J, Capovilla A, Venter W D, Stevens W S, Papathanasopoulos M A: Molecular characterization of the HIV type 1 subtype C accessory genes vif, vpr, and vpu. *AIDS Res Hum Retroviruses* 2007, 23:322-330.

Belliard G, Romieu A, Zagury J F, Dali H, Chaloin O, Le Grand R, Loret E, Briand J P, Rogues B, Desgranges C, Muller S. Specificity and effect on apoptosis of Tat antibodies from vaccinated and SHIV-infected rhesus macaques and HIV-infected individuals. *Vaccine.* 2003, 21:3186-3199.

Berkhout B, Silverman R H, Jeang K T. Tat trans-activates the human immunodeficiency virus through a nascent RNA target. *Cell.* 1989, 59:273-282.

1. Bhoopat L, Rithaporn T S, Khunamornpong S, Bhoopat T, Taylor C R, Thorner P S: Cell reservoirs in lymph nodes infected with HIV-1 subtype E differ from subtype B: identification by combined in situ polymerase chain reaction and immunohistochemistry. *Mod Pathol* 2006, 19:255-263.

Bres V, Tagami H, Peloponese J M, Loret E, Jeang K T, Nakatani Y, Emiliani S, Benkirane M, Kiernan R E. Differential acetylation of Tat coordinates its interaction with the co-activators cyclin T1 and PCAF. *EMBO J.* 2002, 21:6811-6819.

Buttò, S., Fiorelli, V., Tripiciano, A., Ruiz-Alvarez, M. J., Scoglio, A., Ensoli, F., Ciccozzi, M., Collacchi, B., Sabbatucci, M., Cafaro, A., Guzman, C. A., Borsetti, A., Caputo, A., Vardas, E., Colvin, M., Lukwiya, M., Rezza, G., Ensoli, B. and the Tat Multicentric Study Group. Sequence conservation and antibody cross-recognition of clade B human immunodeficiency virus (HIV) type 1 Tat protein in HIV-1-infected Italians, Ugandans, and South Africans. *J. Infect. Dis.* 2003, 188: 1171-1180.

Cafaro, A., Caputo, A., Fracasso, C., Maggiorella, M. T., Goletti, D., Baroncelli, S., Pace, M., Sernicola, L., Koanga-Mogtomo, M. L., Betti, M., Borsetti, A., Belli, R., Akerblom, L., Corrias, F., Butto, S., Heeney, J., Verani, P., Titti, F. and Ensoli, B. Control of SHIV-89.6P-infection of cynomolgus monkeys by HIV-1 Tat protein vaccine. *Nat. Med.* 1999, 6: 643-650.

Cafaro, A., Titti, F., Fracasso, C., Maggiorella, M. T., Baroncelli, S., Caputo, A., Goletti, D., Borsetti, A., Pace, M., Fanales-Belasio, E., Ridolfi, B., Negri, D. R., Sernicola, L., Belli, R., Corrias, F., Macchia, I., Leone, P., Michelini, Z., Ten Haaft, P., Butto, S., Verani, P., and Ensoli, B. Vaccination with DNA containing that coding sequences and unmethylated CpG motifs protects cynomolgus monkeys upon infection with simian/human immunodeficiency virus (SHIV89.6P) *Vaccine* 2001, 19: 2862-2877.

Campbell G R, Pasquier E, Watkins J, Bourgarel-Rey V, Peyrot V, Esquieu D, Barbier P, de Mareuil J, Braguer D, Kaleebu P, Yirrell D L, Loret E P. The glutamine-rich region of the HIV-1 Tat protein is involved in T-cell apoptosis. *J Biol Chem.* 2004, 279:48197-48204.

Campbell G R, Senkaali D, Watkins J, Esquieu D, Opi S, Yirrell D L, Kaleebu P, Loret E P: Tat mutations in an African cohort that do not prevent transactivation but change its immunogenic properties *Vaccine* 2007, 25:8441-8417.

Campbell G R, Watkins J D, Esquieu D, Pasquier E, Loret E P, Spector S A: The C-terminus of HIV-1 Tat modulates the extent of CD178 mediated apoptosis of T cells. *J Biol Chem* 2005, 280:38376-38382.

Campbell G R, Watkins J D, Singh K K, Loret E P, Spector S A: Human immunodeficiency virus type 1 subtype C Tat fails to induce intracellular calcium flux and induces reduced tumor necrosis factor production from monocytes. *J Virol* 2007, 81:5919-5928.

Carr J K, Salminen M O, Koch C, Gotte D, Artenstein A W, Hegerich P A, St Louis D, Burke D S, McCutchan F E. Full-length sequence and mosaic structure of a human immunodeficiency virus type 1 isolate from Thailand. J Virol. 1996, 9, 5935-5943.

Caselli, E., Betti, M., Grossi, M. P., Balboni, P. G., Rossi, C., Boarini, C., Cafaro, A., Barbanti-Brodano, G., Ensoli, B. and Caputo, A. DNA immunization with HIV-1 that mutated in the trans activation domain induces humoral and cellular immune responses against wild-type Tat. *J. Immunol.* 1999, 162: 5631-5638.

Chang H C, Samaniego F, Nair B C, Buonaguro L, Ensoli B: HIV-1 Tat protein exits from cells via a leaderless secretory pathway and binds to extracellular matrix-associated heparan sulfate proteoglycans through its basic region. *AIDS* 1997, 11:1421-1431.

Chen D, Wang M, Zhou S, Zhou Q. HIV-1 Tat targets microtubules to induce apoptosis, a process promoted by the pro-apoptotic Bcl-2 relative Bim. *EMBO J.* 2002, 21:6801-6810.

Coetzer M, Cilliers T, Ping L H, Swanstrom R, Morris L: Genetic characteristics of the V3 region associated with CXCR4 usage in HIV-1 subtype C isolates. *Virology* 2006, 356:95-105.

Cohen S S, Li C, Ding L, Cao Y, Pardee A B, Shevach E M, Cohen D I. Pronounced acute immunosuppression in vivo mediated by HIV Tat challenge. *Proc Natl Acad Sci USA.* 1999, 96:10842-10847.

Cullen B R: The HIV-1 Tat protein: an RNA sequence-specific processivity factor? *Cell* 1990, 63:655-657.

de Mareuil J, Carre M, Barbier P, Campbell G R, Lancelot S, Opi S, Esquieu D, Watkins J D, Prevot C, Braguer D, Peyrot V, Loret E P. HIV-1 Tat protein enhances microtubule polymerization. *Retrovirology.* 2005, 2:5.

Delaporte, E., Dupont, A., Merlin, M., Josse, R., Hamono, B., Larouze, B. & Brun-Vezinet, F. Seroepidemiological survey of HIV-1 and HIV-2 antibodies in Gabon. *AIDS* 1988, 2: 136-137.

Delaporte, E., Janssens, W., Peeters, M., Buve, A., Dibanga, G., Perret, J. L., Ditsambou, V., Mba, J. R., Courbot, M. C., Georges, A., Bourgeois, A., Samb, B., Henzel, D., Heyndrickx, L., Fransen, K., Van der Groen, G. & Larouze, B. Epidemiological and molecular characteristics of HIV infection in Gabon, 1986-1994. *AIDS* 1996, 8: 903-910.

Ensoli B, Barillari G, Salahuddin S Z, Gallo R C, Wong-Staal F. Tat protein of HIV-1 stimulates growth of cells derived from Kaposi's sarcoma lesions of AIDS patients. *Nature.* 1990, 345:84-86.

Feinberg M B & Moore J P. AIDS vaccine models: challenging challenge viruses. *Nat Med* 2002, 8: 207-210.

Fisher A G, Ratner L, Mitsuya H, Marselle L M, Harper M E, Broder S, Gallo R C, Wong-Staal F. Infectious mutants of HTLV-III with changes in the 3' region and markedly reduced cytopathic effects. *Science.* 1986, 233:655-659.

Fittipaldi A, Ferrari A, Zoppé M, Arcangeli C, Pellegrini V, Beltram F, Giacca M: Cell membrane lipid rafts mediate caveolar endocytosis of HIV-1 Tat fusion proteins. *J Biol Chem* 2003, 278:34141-34149.

Fujisawa J, Seiki M, Kiyokawa T, Yoshida M: Functional activation of the Long Terminal Repeat of Human T cell leukemia virus type I by a trans-acting factor. *Proc Natl Acad Sci USA* 1985, 82: 2277-2281.

Gallo R C: Tat as one key to HIV-induced immune pathogenesis and Tat toxoid as an important component of a vaccine. *Proc Natl Acad Sci USA* 1999, 96:8324-8326.

Goldstein G: HIV-1 Tat protein as a potential AIDS vaccine. *Nat Med* 1996, 9:960-964.

Goldstein, G., Manson, K., Tribbick, G. & Smith, R. Minimization of chronic plasma viremia in rhesus macaques immunized with synthetic HIV-1 Tat peptides and infected with a chimeric simian/human immunodeficiency virus (SHIV33). *Vaccine* 2000, 25: 2789-2795.

Gregoire C, Peloponese J M Jr, Esquieu D, Opi S, Campbell G, Solomiac M, Lebrun E, Lebreton J, Loret E P. Homonuclear (1)H-NMR assignment and structural characterization of human immunodeficiency virus type 1 Tat Mal protein. *Biopolymers.* 2001, 62:324-335.

Gregoire C J, Loret E P. Conformational heterogeneity in two regions of TAT results in structural variations of this protein as a function of HIV-1 isolates. *J Biol Chem.* 1996, 271:22641-22646.

Hemelaar J, Gouws E, Ghys P D, Osmanov S Global and regional distribution of HIV-1 genetic subtypes and recombinants in 2004. *AIDS.* 2006, 20:13-23.

Huet, T., Dazza, M. C., Brun-Vezinet, F., Roelants, G. E. & Wain-Hobson, S. A highly defective HIV-1 strain isolated from a healthy Gabonese individual presenting an atypical western blot. *AIDS.* 1989, 3: 707-715.

Jeang K T, Xiao H, Rich E A. Multifaceted activities of the HIV-1 transactivator of transcription, Tat. *J Biol Chem.* 1999; 274:28837-28840. Review.

Jennes, W., Verheyden, S., Demanet, C., Adje-Toure, C. A., Vuylsteke, B., Nkengasong, J. N., Kestens, L. Cutting Edge: Resistance to HIV-1 Infection among African Female Sex Workers Is Associated with Inhibitory KIR in the Absence of Their HLA Ligands. *J Immunol.* 2006, 177: 6588-6592.

Kaleebu P, Nankya I L, Yirrell D L, Shafer L A, Kyosiimire-Lugemwa J, Lule D B, Morgan D, Beddows S, Weber J, Whitworth J A: Relation between chemokine receptor use, disease stage, and HIV-1 subtypes A and D: results from a rural Ugandan cohort. *J Acquir Immune Defic Syndr* 2007, 45:28-33.

Kaul, R., Rowland-Jones, S. L., Kimani, J., Dong, T., Yang, H. B., Kiama, P., Rostron, T., Njagi, E., Bwayo, J. J., MacDonald, K. S., McMichael, A. J., Plummer, F. A. Late seroconversion in HIV-resistant Nairobi prostitutes despite pre-existing HIV-specific CD8+ responses. *J Clin Invest.* 2001, 107: 341-349.

Kuiken C, Leitner T, Foley B, Hahn B, Marx P, McCutchan F, Wolinsky S, Korber B, (Eds). HIV Sequence Compendium. *Theoretical Biology and Biophysics Group, Los Alamos National Laboratory*, NM, LA-UR 06-0680; 2008.

Kuppuswamy M, Subramania T, Srinivasan A, Chinnadurai G: Multiple functional domains of Tat the trans-activator of HIV-1 defined by mutational analysis. *Nucl Acid Res* 1989, 17:3551-3561.

Lan N T, Recordon-Pinson P, Hung P V, Uyen N T, Lien T T, Tien H T, Garrigue I, Schrive M H, Pellegrin I, Lafon M E, Aboulker J P, Barre-Sinousi F, Fleury H J. HIV type 1 isolates from 200 untreated individuals in Ho Chi Minh City (Vietnam): ANRS 1257 Study. Large predominance of CRF01_AE and presence of major resistance mutations to antiretroviral drugs. *AIDS Res Hum Retroviruses.* 2003, 19:925-928.

Levy J A. HIV pathogenesis: knowledge gained after two decades of research. *Adv Dent Res.* 2006, 19:10-16. Review Liang X, Casimiro D R, Schleif W A, Wang F, Davies M E, Zhang Z Q, Fu T M, Finnefrock A C, Handt L, Citron M P, Heidecker G, Tang A, Chen M, Wilson K A, Gabryelski L, McElhaugh M, Carella A, Moyer C, Huang L, Vitelli S, Patel D, Lin J, Emini E A, Shiver J W. Gag and Env but not Tat show efficacy against simian-human immunodeficiency virus 89.6P challenge in Mamu-A*01-negative rhesus monkeys. *J Virol.* 2005, 19: 12321-12331.

Lopalco L, Barassi C, Paolucci C, Breda D, Brunelli D, Nguyen M, Nouhin J, Luong T T, Truong L X, Clerici M, Calori G, Lazzarin A, Pancino G, Burastero S E. Predictive value of anti-cell and anti-human immunodeficiency virus (HIV) humoral responses in HIV-1-exposed seronegative cohorts of European and Asian origin. *J Gen Virol.* 2005, 86:339-348.

Loret E P, Georgel P, Johnson W C Jr, Ho P S. Circular dichroism and molecular modeling yield a structure for the complex of human immunodeficiency virus type 1 trans-activation response RNA and the binding region of Tat, the trans-acting transcriptional activator. *Proc Natl Acad Sci USA.* 1992, 89:9734-9738.

Maggiorella, M. T., Baroncelli, S., Michelini, Z., Fanales-Belasio, E., Moretti, S., Sernicola, L., Cara, A., Negri, D. R., Butto, S., Fiorelli, V., Tripiciano, A., Scoglio, A., Caputo, A., Borsetti, A., Ridolfi, B., Bona, R., ten Haaft, P., Macchia, I., Leone, P., Pavone-Cossut, M. R., Nappi, F., Ciccozzi, M., Heeney, J., Titti, F., Cafaro, A. and Ensoli, B. Long-term protection against SHIV89.6P replication in HIV-1 Tat vaccinated cynomolgus monkeys. *Vaccine* 2004, 22: 3258-3269.

Marmor M, Hertzmark K, Thomas S M, Halkitis P N, Vogler M. Resistance to HIV infection. *J Urban Health.* 2006, 83:5-17. Review.

McMichael A J, Rowland-Jones S L. Cellular immune responses to HIV. *Nature.* 2001, 410:980-987. Review.

Mishra M, Vetrivel S, Siddappa N B, Ranga U, Seth P: Clade-specific differences in neurotoxicity of human immunodeficiency virus-1 B and C Tat of human neurons: significance of dicysteine C30C31 motif. *Ann Neurol* 2008, 63:366-376.

Nguyen, M., Pean, P., Lopalco, L., Nouhin, J., Phoung, V., Ly, N., Vermisse, P., Henin, Y., Barre-Sinoussi, F., Burastero, S. E., Reynes, J. M., Carcelain, G., Pancino, G. HIV-specific antibodies but not T cell responses are associated with protection in seronegative partners of HIV-1-infected individuals in Cambodia. *J Acquir Immune Defic Syndr.* 2006, 42: 412-419.

Opi S, Peloponese J M Jr, Esquieu D, Campbell G, de Mareuil J, Walburger A, Solomiac M, Gregoire C, Bouveret E, Yirrell D L, Loret E P. Tat HIV-1 primary and tertiary structures critical to immune response against non-homologous variants. *J Biol Chem.* 2002, 277:35915-35919.

Opi S, Peloponese J M Jr, Esquieu D, Watkins J, Campbell G, De Mareuil J, Jeang K T, Yirrell D L, Kaleebu P, Loret E P. Full-length HIV-1 Tat protein necessary for a vaccine. *Vaccine.* 2004, 22:3105-3111.

Opi S, Peloponese J M, Jr, Esquieu D, Campbell G, de Mareuil J, Walburger A, Solomiac M, Gregoire C, Bouveret E, Yirrell D L, Loret E P: Tat HIV-1 primary and tertiary structures critical to immune response against non-homologous variants. *J Biol Chem* 2002, 277:35915-35919.

Osmanov S, Pattou C, Walker N, Schwardlander B, Esparza J; WHO-UNAIDS Network for HIV Isolation and Characterization. Estimated global distribution and regional spread of HIV-1 genetic subtypes in the year 2000. *J Acquir Immune Defic Syndr.* 2002, 29:184-190.

Pacyniak E, Gomez M L, Gomez L M, Mulcahy E R, Jackson M, Hout D R, Wisdom B J, Stephens E B: Identification of a region within the cytoplasmic domain of the subtype B Vpu protein of human immunodeficiency virus type 1 (HIV-1) that is responsible for retention in the golgi complex and its absence in the Vpu protein from a subtype C HIV-1. *AIDS Res Hum Retroviruses* 2005, 21:379-394.

Pauza, C. D., Trivedi, P., Wallace, M., Ruckwardt, T. J., Le Buanec, H., Lu., W, Bizzini, B., Burny, A., Zagury, D. & Gallo, R. C. Vaccination with tat toxoid attenuates disease in simian/HIV-challenged macaques. *Proc. Natl. Acad. Sci. U.S.A.* 2000, 97: 3515-3519.

Peloponese J M Jr, Collette Y, Gregoire C, Bailly C, Campese D, Meurs E F, Olive D, Loret E P. Full peptide synthesis, purification, and characterization of six Tat variants. Differences observed between HIV-1 isolates from Africa and other continents. *J Biol Chem.* 1999, 274:11473-11478.

Peloponese J M Jr, Gregoire C, Opi S, Esquieu D, Sturgis J, Lebrun E, Meurs E, Collette Y, Olive D, Aubertin A M, Witvrow M, Pannecouque C, De Clercq E, Bailly C, Lebreton J, Loret EP. 1H-13C nuclear magnetic resonance assignment and structural characterization of HIV-1 Tat protein. *C R Acad Sci III.* 2000, 323:883-894.

Péloponèse J M, Grégoire C, Opi S, Esquieu D, Sturgis J, Lebrun E, Meurs E, Collette Y, Olive D, Aubertin A M, Witvrow M, Pannecouque C, De Clercq E, Bailly C, Lebreton J, Loret E P: $^1H$-$^{13}C$ nuclear magnetic resonance assignment and structural characterization of HIV-1 Tat protein *C R Acad Sci III* 2000, 323:883-894.

Plotkin, Vaccines 3rd Ed. Philadelphia, WB Saunders Co. 1999

Poggi A, Carosio R, Spaggiari G M, Fortis C, Tambussi G, Dell'Antonio G, Dal Cin E, Rubartelli A, Zocchi M R. NK cell activation by dendritic cells is dependent on LFA-1-mediated induction of calcium-calmodulin kinase II: inhibition by HIV-1 Tat C-terminal domain. *J Immunol.* 2002, 1:95-101.

Ranga U, Shankarappa R, Siddappa N B, Ramakrishna L, Nagendran R, Mahalingam M, Mahadevan A, Jayasuryan N, Satishchandra P, Shankar S K, Prasad V R: Tat protein of human immunodeficiency virus type 1 subtype C strains is a defective chemokine. *J Virol* 2004, 78:2586-2590.

Ranjbar S, Rajsbaum R, Goldfeld A E: Transactivator of transcription from HIV type 1 subtype E selectively inhibits TNF gene expression via interference with chromatin remodeling of the TNF locus. *J Immunol* 2006, 176:4182-4190.

Re M C, Vignoli M, Furlini G, Gibellini D, Colangeli V, Vitone F, La Placa M. Antibodies against full-length Tat protein and some low-molecular-weight Tat-peptides correlate with low or undetectable viral load in HIV-1 seropositive patients. *J Clin Virol.* 2001, 21:81-89.

Renjifo B, Gilbert P, Chaplin B, Msamanga G, Mwakagile D, Fawzi W, Essex M, and the Tanzanian Vitamin and HIV Study Group: Preferential in-utero transmission of HIV-1 subtype C as compared to HIV-1 subtypes A or D. *AIDS* 2004, 18:1629-1636.

Roof P, Ricci M, Genin P, Montano M A, Essex M, Wainberg M A, Gatignol A, Hiscott J: Differential regulation of HIV-1 clade-specific B, C, and E long terminal repeats by NF-kappaB and the Tat transactivator. *Virology* 2002, 296: 77-83.

Saez-Cirion A, Versmisse P, Truong L X, Chakrabarti L A, Carpentier W, Barre-Sinoussi F, Scott-Algara D, Pancino G. Persistent resistance to HIV-1 infection in CD4 T cells from exposed uninfected Vietnamese individuals is mediated by entry and post-entry blocks. *Retrovirology* 2006, 3: 81-86.

Scott-Algara, D., Truong, L. X., Versmisse, P., David, A., Luong, T. T., Nguyen, N. V., Theodorou, I., Barre-Sinoussi, F., Pancino, G. Cutting edge: increased NK cell activity in HIV-1-exposed but uninfected Vietnamese intravascular drug users. *J Immunol.* 2003, 171: 5663-5667.

Senkaali, D., Kebba, A., Shafer, L. A., Campbell, G., Loret, E., Van der Paal, L., Grosskurth, H., Yirrell, D. & Kaleebu, P. Tat specific binding IgG and disease progression in HIV-1 infected Ugandans *AIDS* 4, 587-94 (2008).

Singh K K, Spector S A. Host Genetic Determinants of HIV Infection and Disease Progression in Children. *Pediatr. Res.* 2009, in press.

Stittelaar, K J, Gruters, R A, Schutten, M, van Baalen, C A, van Amerongen, G, Cranage, M, Liljestrom, P, Sutter, G, Osterhaus, A D. Comparison of the efficacy of early versus late viral proteins in vaccination against SIV. *Vaccine* 2002, 20: 2921-2927.

Tran H K, Chartier L, Troung L X, Nguyen N N, Fontanet A, Barre-Sinoussi F E, Pancino G, Scott-Algara D. Systemic immune activation in HIV-1-exposed uninfected Vietnamese intravascular drug users. *AIDS Res Hum Retroviruses.* 2006, 22:255-261.

Truong L X, Luong T T, Scott-Algara D, Versmisse P, David A, Perez-Bercoff D, Nguyen N V, Tran H K, Cao C T, Fontanet A, Follezou J Y, Theodorou I, Barre-Sinoussi F, Pancino G. CD4 cell and CD8 cell-mediated resistance to HIV-1 infection in exposed uninfected intravascular drug users in Vietnam. *AIDS.* 2003, 17:1425-1434.

Van Baalen C A, Pontesilli O, Huisman R C, Geretti A M, Klein M R, de Wolf F, Miedema F, Gruters R A, Osterhaus A D: Human immunodeficiency virus type 1 Rev- and Tat-specific cytotoxic T lymphocyte frequencies inversely correlate with rapid progression to AIDS. *J. Gen Virol.* 1997, 78: 1913-1918.

Vanichseni S, Tappero J W, Pitisuttithum P, Kitayaporn D, Mastro T D, Vimutisunthorn E, van Griensvan F, Heyward W L, Francis D P, Choopanya K; Bangkok Vaccine Evaluation Group. Recruitment, screening and characteristics of injection drug users participating in the AIDSVAX B/E HIV vaccine trial, Bangkok, Thailand. *AIDS* 2004, 18: 311-316.

Vasan A, Renjifo B, Hertzmark E, Chaplin B, Msamanga G, Essex M, Fawzi W, Hunter D: Different rates of disease progression of HIV type 1 infection in Tanzania based on infecting subtype. *Clin Infect Dis* 2006, 42:843-852.

Vendeville A, Rayne F, Bonhoure A, Bettache N, Montcourrier P, Beaumelle B: HIV-1 Tat enters T cells using coated pits before translocating from acidified endosomes and eliciting biological responses. *Mol Biol Cell* 2004, 15:2347-2360.

Verrier B, Le Grand R, Ataman-Onal Y, Terrat C, Guillon C, Durand P Y, Hurtrel B, Aubertin A M, Sutter G, Erfle V, Girard M. Evaluation in rhesus macaques of Tat and Rev-targeted immunization as a preventive vaccine against mucosal challenge with SHIV-BX08. *DNA Cell Biol* 2002, 21: 653-658.

Wadia J S, Stan R V, Dowdy S F: Transducible TAT-HA fusogenic peptide enhances escape of TAT-fusion proteins after lipid raft macropinocytosis. *Nat Med* 2004, 10:310-315.

Walker P R, Ketunuti M, Choge I A, Meyers T, Gray G, Holmes E C, Morris L: Polymorphisms in Nef associated with different clinical outcomes in HIV type 1 subtype C-infected children. *AIDS Res Hum Retroviruses* 2007, 23:204-215.

Watkins J, Campbell G R, Halimi H, Loret E P: Homonuclear $^1$H NMR and Circular Dichroism Study of the HIV-1 Tat Eli variant. *Retrovirology* 2008, 5:83.

Watkins J D, Lancelot S, Campbell G R, Esquieu D, de Mareuil J, Opi S, Annappa S, Salles J P, Loret E P. Reservoir cells no longer detectable after a heterologous SHIV challenge with the synthetic HIV-1 Tat Oyi vaccine. *Retrovirology.* 2006, 3:8.

Westendorp M O, Frank R, Ochsenbauer C, Stricker K, Dhein J, Walczak H, Debatin K M, Krammer P H. Sensitization of T cells to CD95-mediated apoptosis by HIV-1 Tat and gp120. *Nature.* 1995, 375:497-500.

Wolf D, Witte V, Laffert B, Blume K, Stromer E, Trapp S, d'Aloja P, Schurmann A, Baur A S. HIV-1 Nef associated PAK and PI3-kinases stimulate Akt-independent Bad-phosphorylation to induce anti-apoptotic signals. *Nat Med.* 2001, 7:1217-1224.

Wong-Staal F, Gallo R C, Chang N T, Ghrayeb J, Papas T S, Lautenberger J A, Pearson M L, Petteway S R, Jr, Ivanoff L, Baumeister K, Whitehorn E A, Rafalski J A, Doran J R, Josephs S J, Starcich B, Livak K J, Patarca R, Haseltine W A, Ratner L: Complete nucleotide sequence of the AIDS virus HTLV-III. *Nature* 1985, 313:277-284.

Xiao H, Neuveut C, Tiffany H L, Benkirane M, Rich E A, Murphy P M, Jeang K T: Selective CXCR4 antagonism by Tat: implications for in vivo expansion of coreceptor use by HIV-1 2000 *Proc Natl Acad Sci USA* 2000, 97:11466-11471.

Zagury J F, Sill A, Blattner W, Lachgar A, Le Buanec H, Richardson M, Rappaport J, Hendel H, Bizzini B, Gringeri A, Carcagno M, Criscuolo M, Burny A, Gallo R C, Zagury D: Antibodies to the HIV-1 Tat protein correlated with nonprogression to AIDS: a rationale for the use of Tat toxoid as an HIV-1 vaccine. *J. Hum. Virol.* 1998, 1:282-292.

The invention claimed is:

1. A pharmaceutical composition, comprising a protein comprising amino acid sequence SEQ ID NO: 1 or SEQ ID NO:2 capable of stimulating an immune response against Tat protein and capable of transactivation, in combination with a pharmaceutically acceptable carrier.

2. The pharmaceutical composition of claim 1, wherein the protein is capable of stimulating an immune response against 2, 3, 4, or more HIV-1 subtypes.

3. The pharmaceutical composition of claim 2, wherein the protein is capable of stimulating an immune response against five HIV-1 subtypes.

4. An immunogenic composition comprising as an active ingredient a transactivation competent Tat Oyi protein comprising a Cysteine at position 22.

5. The immunogenic composition of claim 4, wherein the protein is selected from SEQ ID NO: 1 or SEQ ID NO: 2.

6. The immunogenic composition of claim 4, further comprising an adjuvant.

7. A method of inducing an anti-HIV immune response in a host, comprising injecting an effective amount of a protein comprising at least one of SEQ ID NO: 1 or SEQ ID NO: 2 and an adjuvant.

8. The method of claim 7, further comprising the step of determining whether the protein triggers an immune response against five or more HIV-1 subtypes, wherein the protein stimulates an immune response against Tat proteins from at least five HIV-1 subtypes.

* * * * *

SEQUENCE LISTING

```
<160> NUMBER OF SEQ ID NOS: 2

<210> SEQ ID NO 1
<211> LENGTH: 77
<212> TYPE: PRT
<213> ORGANISM: Human immunodeficiency virus type 1

<400> SEQUENCE: 1

Trp Lys His Pro Gly Ser Gln Pro Lys Thr Ala Cys Asn Asn Cys Tyr
1               5                   10                  15

Cys Lys Arg Cys Cys Leu His Cys Gln Val Cys Phe Thr Lys Lys Gly
            20                  25                  30

Leu Gly Ile Ser Tyr Gly Arg Lys Lys Arg Gln Arg Arg Arg Ala
        35                  40                  45

Pro Gln Asp Ser Lys Thr His Gln Val Ser Leu Ser Lys Gln Pro Ala
    50                  55                  60

Ser Gln Pro Arg Gly Asp Pro Thr Gly Pro Lys Glu Ser
65                  70                  75

<210> SEQ ID NO 2
<211> LENGTH: 101
<212> TYPE: PRT
<213> ORGANISM: Human immunodeficiency virus type 1

<400> SEQUENCE: 2

Met Glu Pro Val Asp Pro Arg Leu Glu Pro Trp Lys His Pro Gly Ser
1               5                   10                  15

Gln Pro Lys Thr Ala Cys Asn Asn Cys Tyr Cys Lys Arg Cys Cys Leu
            20                  25                  30

His Cys Gln Val Cys Phe Thr Lys Lys Gly Leu Gly Ile Ser Tyr Gly
        35                  40                  45

Arg Lys Lys Arg Arg Gln Arg Arg Arg Ala Pro Gln Asp Ser Lys Thr
    50                  55                  60

His Gln Val Ser Leu Ser Lys Gln Pro Ala Ser Gln Pro Arg Gly Asp
65                  70                  75                  80

Pro Thr Gly Pro Lys Glu Ser Lys Lys Lys Val Glu Arg Glu Thr Glu
            85                  90                  95

Thr Asp Pro Glu Asp
            100
```